(12) United States Patent
Evans et al.

(10) Patent No.: US 8,968,317 B2
(45) Date of Patent: *Mar. 3, 2015

(54) SURGICAL FORCEPS

(75) Inventors: Allan J. Evans, Golden, CO (US); Peter M. Mueller, Frederick, CO (US); Peter D. Gadsby, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 817 days.

This patent is subject to a terminal disclaimer.

(21) Appl. No.: 13/212,297

(22) Filed: Aug. 18, 2011

(65) Prior Publication Data
US 2013/0046306 A1    Feb. 21, 2013

(51) Int. Cl.
A61B 18/12 (2006.01)
A61B 18/14 (2006.01)
A61B 18/00 (2006.01)

(52) U.S. Cl.
CPC ..... *A61B 18/1445* (2013.01); *A61B 2018/0063* (2013.01); *A61B 2018/1452* (2013.01); *A61B 2018/1455* (2013.01)
USPC .............................................. 606/52; 606/51

(58) Field of Classification Search
CPC .................. A61B 18/1445; A61B 2018/0063; A61B 2018/1452; A61B 2018/145; A61B 17/28
USPC .................................... 606/27, 34, 41, 51–52
See application file for complete search history.

(56) References Cited

U.S. PATENT DOCUMENTS

| | | | |
|---|---|---|---|
| 4,041,952 A | * | 8/1977 | Morrison et al. ............... 606/42 |
| D249,549 S | | 9/1978 | Pike |
| 4,120,302 A | | 10/1978 | Ziegler |
| D263,020 S | | 2/1982 | Rau, III |
| D295,893 S | | 5/1988 | Sharkany et al. |
| D295,894 S | | 5/1988 | Sharkany et al. |
| D298,353 S | | 11/1988 | Manno |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Daniel Fowler

(57) ABSTRACT

A forceps includes an end effector assembly including first and second jaw members. One or both of the jaw members is moveable relative to the other between a spaced-apart position and an approximated position for grasping tissue therebetween. One or both of the jaw members includes a jaw frame including an engagement recess defined on each lateral side thereof and a replaceable component configured for slidable positioning about the jaw frame. The replaceable component includes an outer jaw housing having an engagement tang disposed on each lateral side thereof. The engagement tangs are configured to engage the engagement recesses of the jaw frame upon slidable positioning of the replaceable component about the jaw frame to secure the replaceable component to the jaw frame. The replaceable component includes an electrically conductive tissue sealing plate engaged to the outer jaw housing to define a tissue sealing surface.

14 Claims, 12 Drawing Sheets

(56) References Cited

U.S. PATENT DOCUMENTS

| | | | |
|---|---|---|---|
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,728,121 A | 3/1998 | Bimbo et al. | |
| H1745 H | 8/1998 | Paraschac | |
| D402,028 S | 12/1998 | Grimm et al. | |
| D408,018 S | 4/1999 | McNaughton | |
| 5,916,213 A * | 6/1999 | Haissaguerre et al. | 606/41 |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| 6,293,954 B1 | 9/2001 | Fogarty et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,406,485 B1 | 6/2002 | Hossain et al. | |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| D493,888 S | 8/2004 | Reschke | |
| 6,773,434 B2 | 8/2004 | Ciarrocca | |
| D496,997 S | 10/2004 | Dycus et al. | |
| D499,181 S | 11/2004 | Dycus et al. | |
| D502,994 S | 3/2005 | Blake, III | |
| 6,932,825 B2 | 8/2005 | Anderson | |
| D509,297 S | 9/2005 | Wells | |
| D525,361 S | 7/2006 | Hushka | |
| D531,311 S | 10/2006 | Guerra et al. | |
| 7,118,570 B2 | 10/2006 | Tetzlaff et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,422,591 B2 | 9/2008 | Phan | |
| D582,038 S | 12/2008 | Swoyer et al. | |
| 7,632,269 B2 | 12/2009 | Truckai et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,744,623 B2 | 6/2010 | Anderson | |
| 7,753,908 B2 | 7/2010 | Swanson | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,877,853 B2 * | 2/2011 | Unger et al. | 29/592.1 |
| 2003/0018331 A1 * | 1/2003 | Dycus et al. | 606/48 |
| 2003/0109875 A1 | 6/2003 | Tetzlaff et al. | |
| 2003/0158548 A1 | 8/2003 | Phan et al. | |
| 2003/0171747 A1 | 9/2003 | Kanehira et al. | |
| 2009/0125012 A1 | 5/2009 | Rioux et al. | |
| 2010/0087814 A1 | 4/2010 | Desinger et al. | |
| 2010/0305567 A1 | 12/2010 | Swanson | |
| 2011/0073246 A1 * | 3/2011 | Brandt et al. | 156/242 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009 165 | 10/2007 |
| DE | 20 2007 009 317 | 10/2007 |
| DE | 20 2007 016 233 | 3/2008 |
| DE | 19738457 | 1/2009 |
| DE | 10 2008 018 406 | 7/2009 |
| EP | 1159926 | 12/2001 |
| EP | 2238938 A1 | 10/2010 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | 99-23933 A2 | 5/1999 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 920, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Homer.
U.S. Appl. No. 12/769,444, filed Apr. 28, 2010, Glenn A. Horner.

(56) References Cited

OTHER PUBLICATIONS

U.S. Appl. No. 12/770,369, filed Apr. 29, 2010, Glenn A. Homer.
U.S. Appl. No. 12/770,380, filed Apr. 29, 2010, Glenn A. Homer.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Homer.
U.S. Appl. No. 12/792,051, filed Jun. 2, 2010, David M. Garrison.
U.S. Appl. No. 12/792,068, filed Jun. 2, 2010, Glenn A. Homer.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John. R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report E 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.

(56) References Cited

OTHER PUBLICATIONS

Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS

BACKGROUND

1. Technical Field

The present disclosure relates to a surgical forceps and, more particularly, to a surgical forceps for sealing and/or cutting tissue.

2. Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

Generally, surgical instruments, including forceps, can be classified as single-use instruments, e.g., instruments that are discarded after a single use, partially-reusable instruments, e.g., instruments including both replaceable portions and portions that are sterilizable for reuse, and completely reusable instruments, e.g., instruments that are completely sterilizable for repeated use. As can be appreciated, those instruments (or components of instruments) that can be sterilized and reused help reduce the costs associated with the particular surgical procedure for which they are used. However, although reusable surgical instruments and surgical instruments with replaceable components are cost-effective, it is important that these instruments be capable of performing the same functions as their single-use counterparts and that any replaceable components of these instruments be removable and replaceable with new components efficiently and easily.

SUMMARY

In accordance with one embodiment of the present disclosure, a forceps is provided. The forceps includes an end effector assembly including first and second jaw members. One or both of the jaw members is moveable relative to the other between a spaced-apart position and an approximated position for grasping tissue therebetween. One or both of the jaw members includes a jaw frame having an engagement recess defined on each lateral side thereof. A replaceable component is configured for slidable positioning about the jaw frame and includes an outer jaw housing having an engagement tang disposed on each lateral side thereof. The engagement tangs are configured to engage the engagement recesses of the jaw frame upon slidable positioning of the replaceable component about the jaw frame to secure the replaceable component to the jaw frame. The replaceable component further includes an electrically conductive tissue sealing plate engaged to the outer jaw housing to define a tissue sealing surface.

In one embodiment, the tissue sealing plate and the outer jaw housing each include a plurality of complementary protrusions and recesses such that the tissue sealing plate is configured to snap-fittingly engage the outer jaw housing.

In another embodiment, an electrical connection member is provided. The electrical connection member is adapted to connect to a source of electrosurgical energy and is coupled to the jaw frame. The electrical connection member includes one or more electrical contacts for supplying electrosurgical energy to the tissue sealing plate. In embodiments, the electrical connection member is a flex circuit.

The tissue sealing plate may include a finger extending into the outer jaw housing and configured to electrically couple to the electrical contact of the electrical connection member for supplying electrosurgical energy to the tissue sealing plate.

In another embodiment, an insulator is disposed within the outer jaw housing and is configured to electrically isolate the tissue sealing plate from the outer jaw housing. Further, the insulator and the outer jaw housing may each include a plurality of protrusions and recesses engageable with one another to retain the insulator in position within the outer jaw housing.

In yet another embodiment, a knife assembly is provided. The knife assembly includes a knife blade that is longitudinally translatable relative to the jaw members between a retracted position and an extended position for cutting tissue grasped between the jaw members.

In still another embodiment, an electrical cutting insert is provided. The electrical cutting insert is releasably engagable with the replaceable component and is configured to electrically cut tissue grasped between the jaw members.

Another embodiment of a forceps provided in accordance with the present disclosure includes an end effector assembly having first and second jaw members. One or both of the jaw members is moveable relative to the other between a spaced-apart position and an approximated position for grasping tissue therebetween. One or both of the jaw members includes a jaw frame including at least one engagement member defined thereon and a flex circuit disposed thereon. The flex circuit is adapted to connect to a source of electrosurgical energy and includes one or more electrical contacts disposed thereon. A replaceable component is configured for slidable positioning about the jaw frame. The replaceable component includes an outer jaw housing having one or more complementary engagement members configured to engage the engagement member(s) of the jaw frame upon slidable positioning of the replaceable component about the jaw frame to secure the replaceable component to the jaw frame. The replaceable component further includes an electrically conductive tissue sealing plate engaged to the outer jaw housing to define a tissue sealing surface. The tissue sealing plate is configured to couple to one of the electrical contacts of the flex circuit upon slidable positioning of the replaceable component about the jaw frame for providing electrosurgical energy to the tissue sealing plate.

In one embodiment, the tissue sealing plate includes a finger extending into the outer jaw housing that is configured to electrically couple to one of the electrical contact of the flex circuit for supplying electrosurgical energy to the tissue sealing plate.

In another embodiment, an insulator is provided. The insulator is disposed within the outer jaw housing and is configured to electrically isolate the tissue sealing plate from the outer jaw housing.

In yet another embodiment, a knife assembly including a knife blade is provided. The knife blade is longitudinally translatable relative to the jaw members between a retracted position and an extended position for cutting tissue grasped between the jaw members.

In still another embodiment, an electrical cutting insert is provided. The electrical cutting insert is releasably engageable with the replaceable component and is configured to electrically cut tissue grasped between the jaw members. More specifically, the electrical cutting insert may include a finger that is configured to electrically couple to one of the electrical contacts of the flex circuit upon engagement of the electrical cutting insert with the replaceable component for supplying electrosurgical energy to the electrical cutting insert.

In accordance with the present disclosure, another embodiment of a forceps is provided that includes an end effector assembly having first and second jaw members either or both of which are movable relative to the other between a spaced-apart position and an approximated position for grasping tissue therebetween. One or both of the jaw members includes a jaw frame having one or more flanges extending from each lateral side thereof and a male electrical connection member extending from a distal end thereof. The male electrical connection member is adapted to connect to a source of electrosurgical energy. A replaceable component is configured for slidable positioning about the jaw frame and includes an outer jaw housing having a slot defined therein on each lateral side thereof. The slots are configured to receive the flanges upon slidable positioning of the replaceable component about the jaw frame to secure the replaceable component to the jaw frame. The replaceable component further includes an electrically conductive tissue sealing plate and a female electrical connection hub electrically coupled to the tissue sealing plate. The female electrical connection hub is configured to receive the male electrical connection member therein upon slidable positioning of the replaceable component about the jaw frame for providing electrosurgical energy to the tissue sealing plate.

In one embodiment, the jaw frame and the replaceable component define complementary-shaped configurations to facilitate slidable positioning of the replaceable component about the jaw frame.

In another embodiment, an electrical cutting insert is releasably engageable with the replaceable component. The electrical cutting insert is configured to electrically cut tissue grasped between the jaw members.

In yet another embodiment, a knife assembly including a knife blade is provided. The knife blade is longitudinally translatable relative to the jaw members between a retracted position and an extended position for cutting tissue grasped between the jaw members.

In still another embodiment, an insulator is disposed within the outer jaw housing and is configured to electrically isolate the tissue sealing plate from the outer jaw housing.

BRIEF DESCRIPTION OF THE DRAWINGS

Various embodiments of the present disclosure are described herein with reference to the drawings wherein.

DETAILED DESCRIPTION

Figure 1:
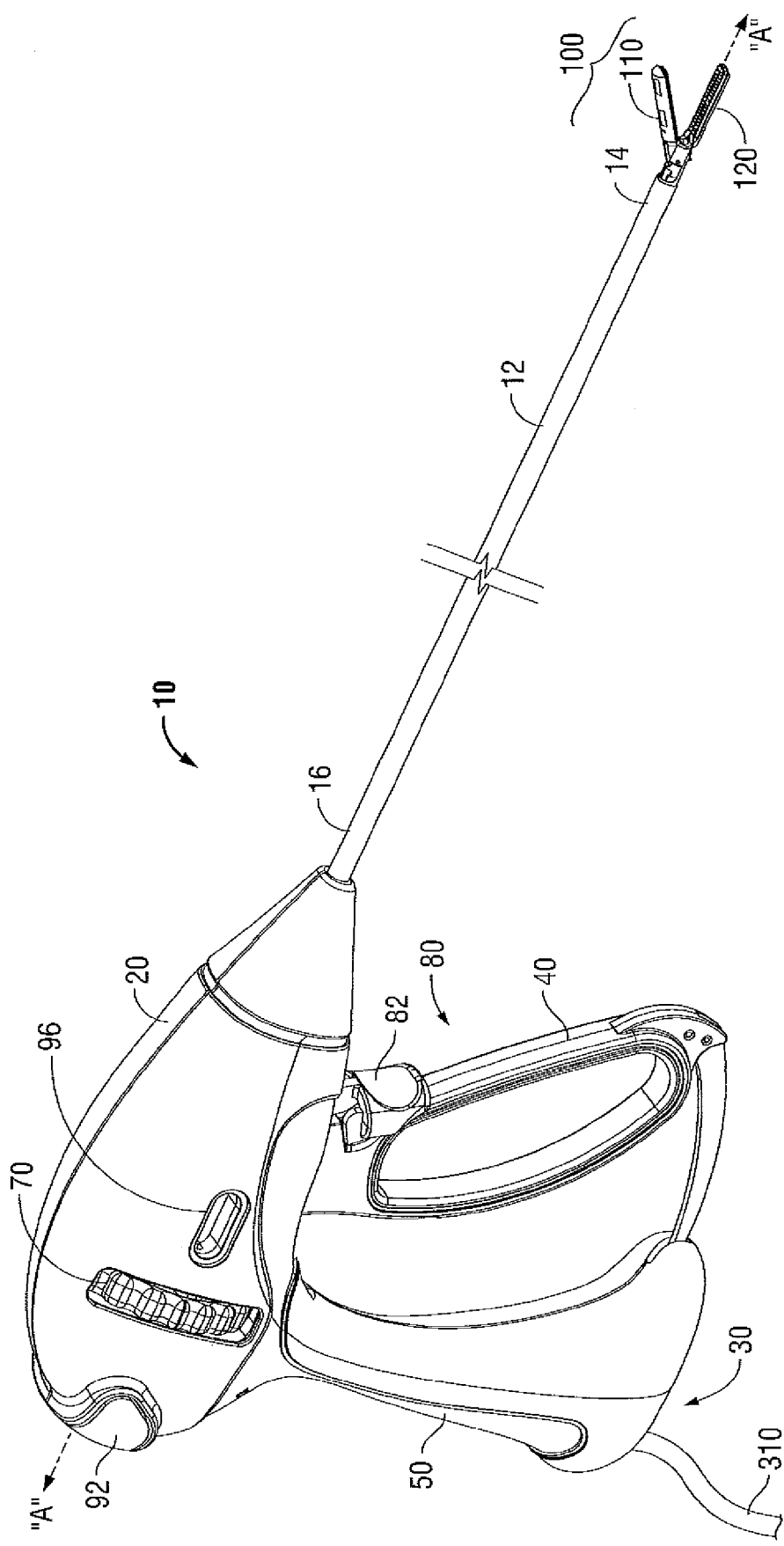
FIG. 1 is a front, perspective view of a surgical forceps configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Referring now to FIG. 1, a forceps 10 for use in connection with endoscopic surgical procedures is shown, although forceps 10 may also be configured for use in connection with traditional open surgical procedures. Forceps 10 defines a longitudinal axis "A-A" and includes a housing 20, a handle assembly 30, a rotating assembly 70, a trigger assembly 80 and an end effector assembly 100. End effector assembly 100 includes first and second jaw members 110, 120, respectively, configured to pivot relative to one another between a spaced-apart position (FIG. 1) and an approximated position (FIG. 8B) for grasping tissue therebetween. Forceps 10 further includes a shaft 12 having a distal end 14 configured to mechanically engage end effector assembly 100 and a proximal end 16 that mechanically engages housing 20. Forceps 10 also includes an electrosurgical cable 310 that connects forceps 10 to a generator (not shown) or other suitable power source, although forceps 10 may alternatively be configured as a battery powered instrument. Cable 310 includes a wire (or wires) (not explicitly shown) extending therethrough and into housing 20 to ultimately connect the source of electrosurgical energy (not explicitly shown) to jaw member 110 and/or jaw member 120 of end effector assembly 100, as will be described in greater detail below.

With continued reference to FIG. 1, handle assembly 30 includes a fixed handle 50 and a moveable handle 40. Fixed handle 50 is integrally associated with housing 20 and handle 40 is moveable relative to fixed handle 50. Rotating assembly 70 is rotatable in either direction about a longitudinal axis "A-A" to rotate end effector 100 about longitudinal axis "A-A." The housing 20 houses the internal working components of the forceps 10.

Figure 2:
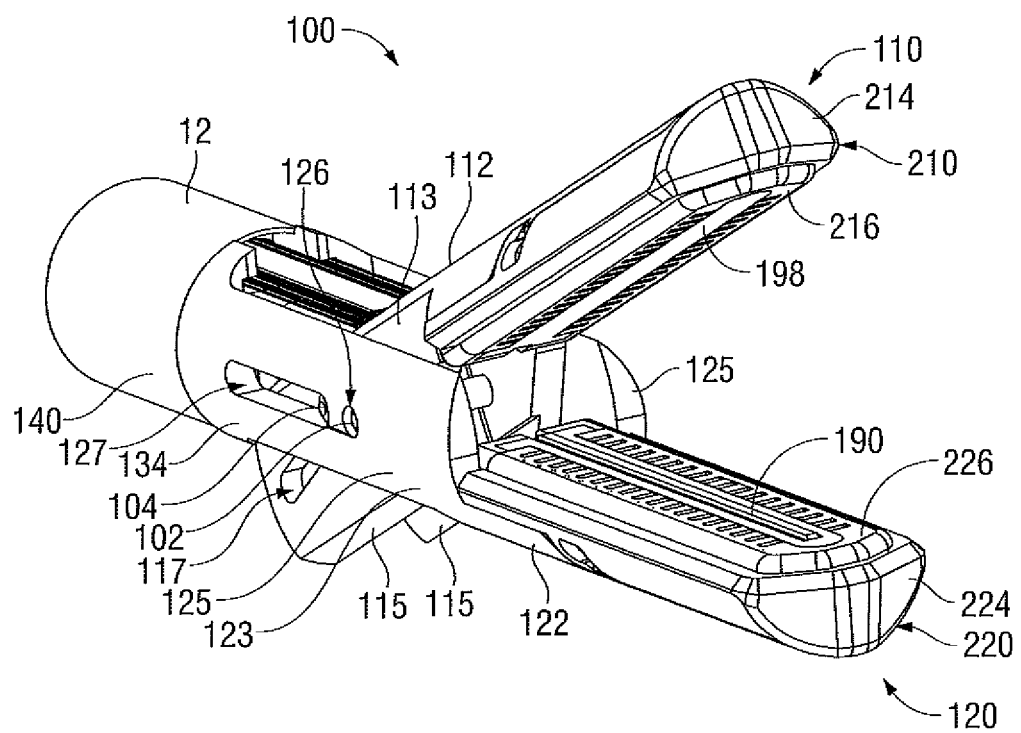
FIG. 2 is a front, perspective view of an end effector assembly configured for use with the forceps of FIG. 1.

Referring momentarily to FIG. 2, end effector assembly 100 is shown attached at a distal end 14 of shaft 12 and includes a pair of opposing jaw members 110 and 120. Each of the first and second jaw members 110, 120 includes a fixed jaw frame 112, 122, respectively, and a replaceable component 210, 220, respectively, selectively engageable with the respective jaw frame 112, 122 to form the fully assembled jaw members 110, 120, respectively. However, jaw members 110, 120 of end effector assembly 100 may also be configured as integral components, e.g., wherein components 210, 220 are fixedly engaged to jaw frames 112, 122 of jaw members 110, 120, respectively.

End effector assembly 100, as shown in FIG. 2, is designed as a unilateral assembly, i.e., where jaw member 120 is fixed relative to shaft 12 and jaw member 110 is moveable relative to both shaft 12 and fixed jaw member 120. However, end effector assembly 100 may alternatively be configured as a bilateral assembly, i.e., where both jaw member 110 and jaw member 120 are moveable relative to one another and with respect to shaft 12.

Figure 8A:
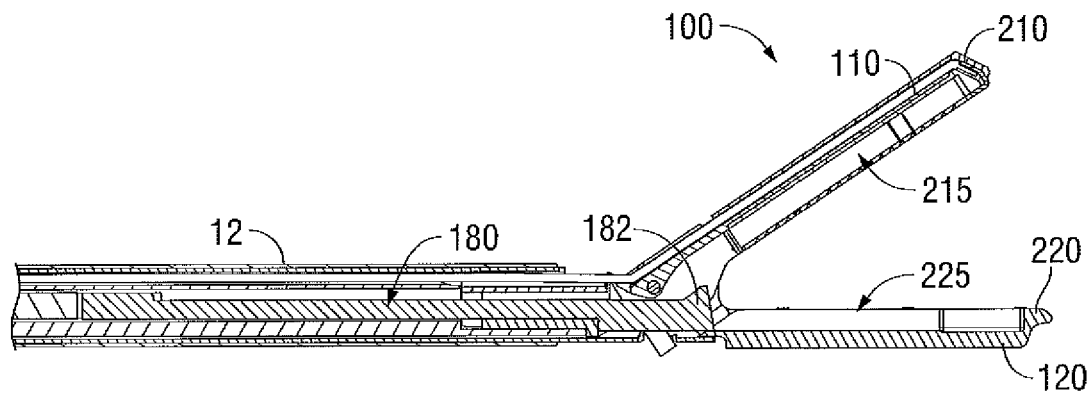
FIG. 8A is a longitudinal, cross-sectional view of the end effector assembly of FIG. 2 with the jaw members disposed in a spaced-apart position.
Figure 8B:
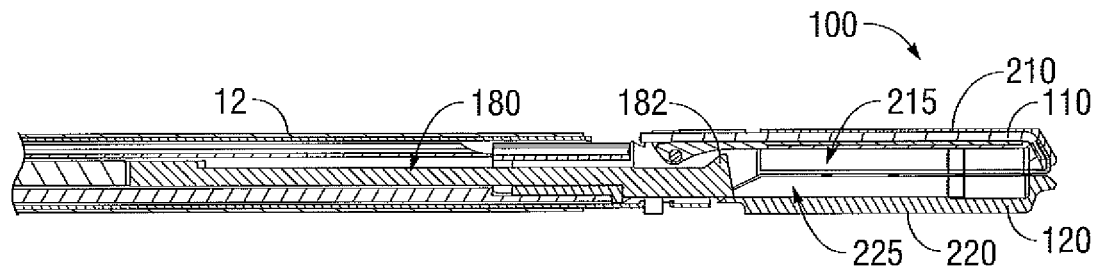
FIG. 8B is a longitudinal, cross-sectional view of the end effector assembly of FIG. 2 with the jaw members disposed in an approximated position and with a knife blade disposed in a retracted position.
Figure 8C:
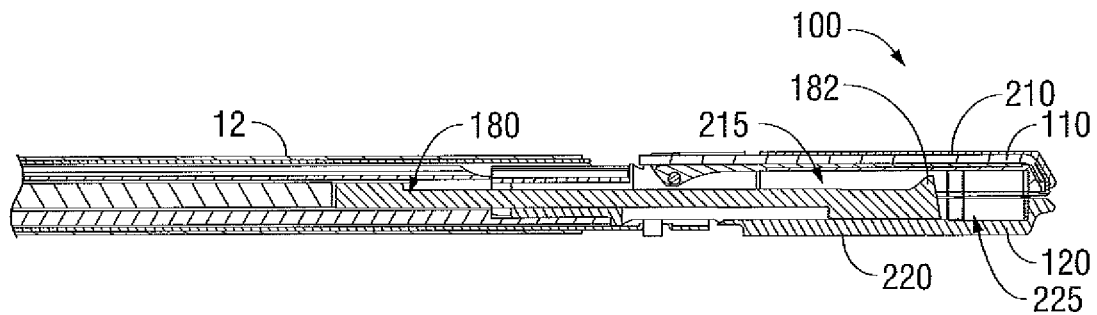
FIG. 8C is a longitudinal, cross-sectional view of the end effector assembly of FIG. 2 with the jaw members disposed in an approximated position and with a knife blade disposed in an extended position.

With continued reference to FIG. 2, each jaw member 110, 120 or, more particularly, the replaceable component 210, 220 of each jaw member 110, 120, respectively, includes an electrically conductive tissue sealing plate 216, 226 disposed thereon. Tissue sealing plates 216, 226 are positioned on jaw members 110, 120, respectively, to define opposed tissue sealing surfaces for grasping and sealing tissue between jaw members 110, 120, as best shown in FIG. 2, and as will be described in greater detail below. In some embodiments, a knife assembly 180 (see FIGS. 8A-8C) is disposed within shaft 12 and a knife channel 215, 225 (FIGS. 8A-8C) is defined within one or both of tissue sealing plates 216, 226, of jaw members 110, 120, respectively, to permit reciprocation of a knife blade 182 (see FIGS. 8A-8C) therethrough for mechanically cutting tissue grasped between jaw members 110, 120. In such an embodiment, trigger 82 of trigger assembly 80 is operable to advance the knife blade 182 (FIGS. 8A-8C) between a retracted position (see FIGS. 8A-8B), wherein knife blade 182 (FIGS. 8A-8C) is disposed within shaft 12, and an extended position (see FIG. 8C), wherein knife blade 182 (FIGS. 8A-8C) extends between jaw members 110, 120 to cut tissue grasped therebetween. Alternatively, end effector assembly 100 may be adapted for electrical cutting via an electrical cutting insert 190, thus obviating the need for knife assembly 180 (FIGS. 8A-8C). Further, end effector assembly 100 may be adapted for both mechanical cutting and electrical cutting, thus allowing a user to select a mode of operation best suited for the particular surgical procedure to be performed. End effector assembly 100, including the various modes of operation and assembly thereof, will be described in greater detail below.

Referring again to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue between sealing plates 216 and 226 of jaw members 110, 120, respectively. As shown in FIG. 1, moveable handle 40 is initially spaced-apart from fixed handle 50 and, correspondingly, jaw members 110, 120 are disposed in the spaced-apart position. Moveable handle 40 is depressible from this initial position to a depressed position corresponding to the approximated position of jaw members 110, 120 (see FIG. 8B).

Figure 3:
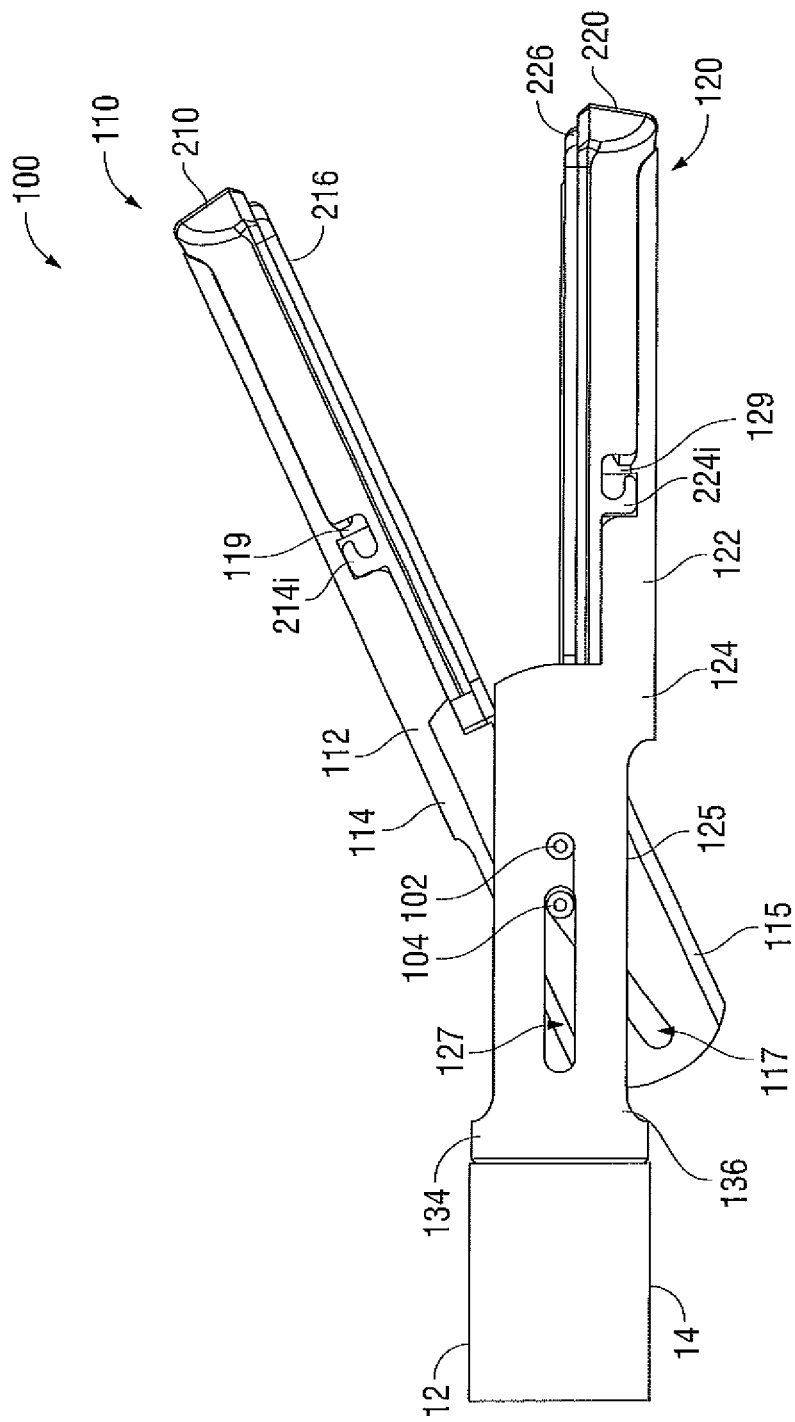
FIG. 3 is a side view of the end effector assembly of FIG. 2.
Figure 4:
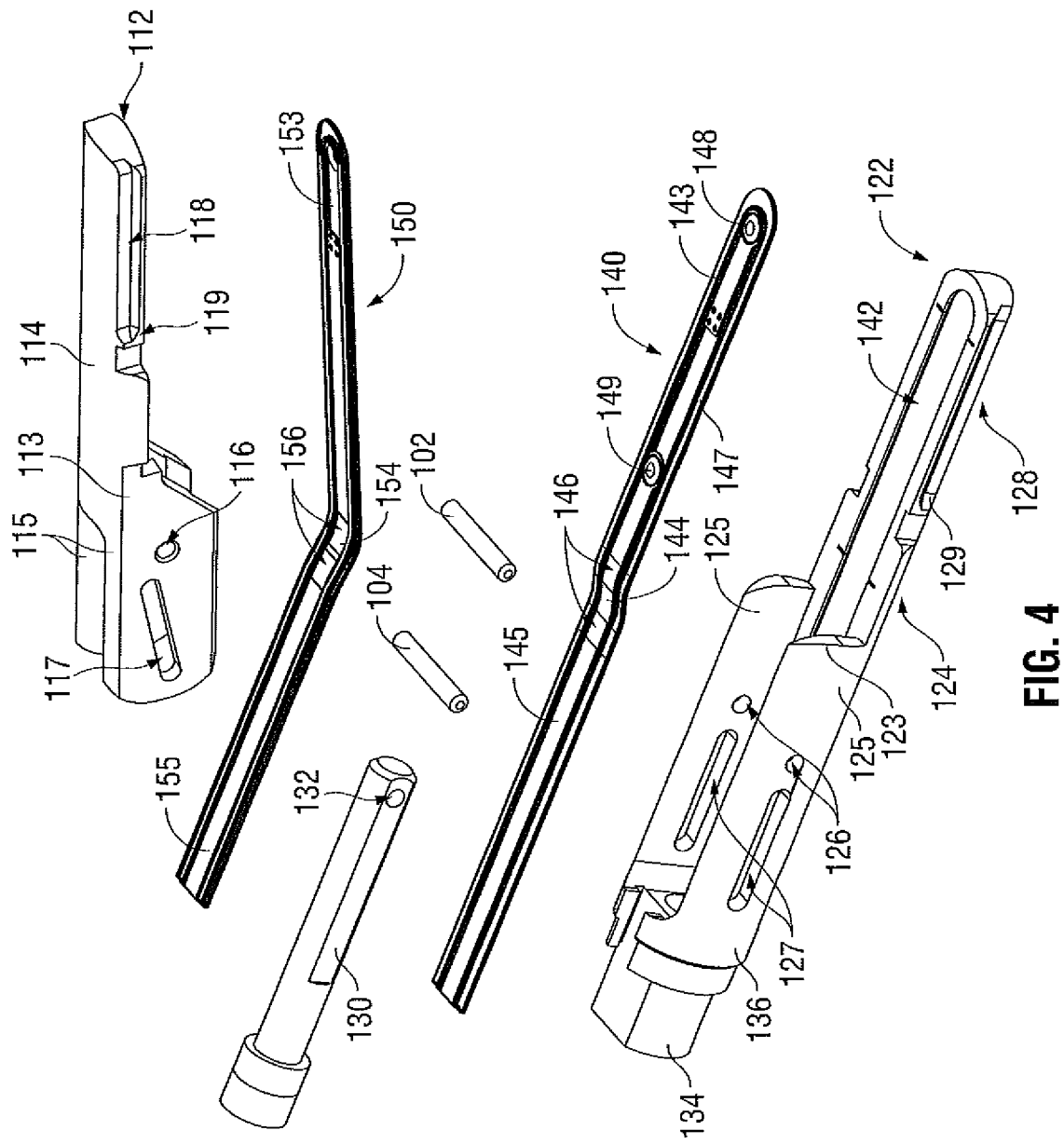
FIG. 4 is a front, perspective view of the end effector assembly of FIG. 2 with parts separated to show the pivotable connection between first and second jaw members of the end effector assembly.

Continuing with reference to FIG. 1, in conjunction with FIGS. 2-4, and as mentioned above, jaw members 110, 120 of end effector assembly 100 each include a respective jaw frame 112, 122. Each jaw frame 112, 122 is monolithically formed as a single component and includes a proximal base 113, 123, respectively, and a distal portion 114, 124, respectively, extending from the respective proximal base 113, 123. Distal portions 114, 124, of jaw frames 112, 122, respectively, are configured to receive replaceable components 210, 220, respectively, thereon, as will be described in greater detail below. Further, distal portion 124 of jaw frame 122 includes a longitudinally-extending recess 142 configured to receive an electrical connection member, e.g., a flex circuit 140, therein. Distal portion 114 of jaw frame 112 may similarly include a recess (not shown) defined therein that is configured to receive a flex circuit 150, or other electrical connection member, although only one of jaw frames 112, 122 need include a flex circuit 150, 140 disposed thereon. Flex circuits 150, 140 of jaw frames 112, 122, respectively, as will be described in greater detail below, extend proximally into shaft 12, ultimately coupling to a source of electrosurgical energy (not explicitly show) for supplying energy to jaw members 110, 120, respectively. However, any other suitable electrical connection member(s) for supplying energy to jaw member 110 and/or jaw member 120 may also be provided.

With continued reference to FIGS. 1-4, and in particular to FIG. 4, proximal base 123 of jaw frame 122 includes a pair of spaced apart flags 125 and a proximal connector 134 disposed at the proximal ends 136 of flags 125. Proximal connector 134 is fixedly engaged to shaft 12, thereby fixing jaw member 120 in position relative to shaft 12. Flags 125 are substantially similar to one another and each include an aperture 126 defined therethrough and a longitudinally-extending slot 127 defined therethrough. Apertures 126 are transversely-aligned with one another and are longitudinally-aligned with slots 127, although apertures 126 may be positioned in other configurations, e.g., offset relative to slots 127. Slots 127 are likewise transversely aligned with one another and extend in a substantially parallel orientation relative to longitudinal axis "A-A." Slots 127 may be centered relative to longitudinal axis "A-A," or may be offset relative to longitudinal axis "A-A" (e.g., above or below longitudinal axis "A-A").

Proximal base 113 of jaw frame 112, similar to proximal base 123 of jaw frame 122, includes a pair of spaced-apart flags 115. Flags 125 of proximal base 123 of jaw frame 122, however, are spaced further apart from one another relative to flags 115 of proximal base 113 of jaw frame 112, such that proximal base 113 of jaw frame 112 is positionable within proximal base 123 of jaw frame 122, e.g., such that flags 115 of jaw frame 112 are positionable between flags 123 of jaw frame 122. This configuration may be reversed, or flags 115 jaw frame 112 and flags 125 of jaw frame 122 may alternatively be spaced-apart a similar distance and may be offset relative to one another. Flags 115 of jaw frame 112 each also include an aperture 116 defined therein and a longitudinally-extending slot 117 defined therethrough. Apertures 116 are transversely aligned with one another and are configured to align with apertures 126 of flags 125 of proximal base 123 of jaw frame 122. Slots 117, on the other hand, are aligned with one another, but are disposed at an oblique angle relative to slots 127 of proximal base 123 of jaw frame 122 and, thus with respect to longitudinal axis "A-A." Slots 117 may alternatively define a splined, or curvate configuration.

With continued reference to FIGS. 1-4, during assembly, with flags 115 of jaw frame 112 disposed between flags 125 of jaw frame 122, a pivot pin 102 is inserted through each pair of apertures 116 and 126 of jaw frames 112, 122, respectively, to pivotably engage jaw frames 112, 122 to one another. Thus, with proximal connector 134 of jaw frame 122 engaging jaw frame 122 to shaft 12, the engagement between pivot pin 102 and apertures 116, 126 of jaw frames 112, 122, respectively, permits jaw frame 112 to pivot relative to jaw frame 122 and, thus, shaft 12, between the spaced-apart position (FIG. 2) and the approximated position (FIG. 8B).

As best shown in FIG. 4, a drive bar 130 is provided for selectively pivoting jaw frames 112, 122 between the spaced-apart position and the approximated position. Drive bar 130 extends from end effector assembly 100 proximally through shaft 12, ultimately coupling to the drive assembly (not explicitly shown) that, in turn, is coupled to handle assembly 30. More specifically, moveable handle 40 of handle assembly 30 is depressible from the initial position to the depressed position to translate drive bar 130 proximally through shaft 12 relative to end effector assembly 100, i.e., towards handle assembly 30. On the other hand, when moveable handle 40 is released, or moved back to the initial position, drive bar 130 is translated distally through shaft 12 relative to end effector assembly 100, i.e., towards end effector assembly 100.

With continued reference to FIG. 4, drive bar 130 includes a distal aperture 132 defined therethrough. During assembly, distal aperture 132 of drive bar 130 is aligned with slots 117 of flags 115 of jaw frame 112 and slots 127 of flags 125 of jaw frame 122 and a pin 104 is inserted therethrough, thereby coupling drive bar 130 to jaw frames 112, 122. Thus, as drive bar 130 is translated proximally, e.g., upon depression of moveable handle 40 relative to fixed handle 50, pin 104 is likewise translated proximally along slots 117 of flags 115 of jaw frame 112 and slots 127 of flags 125 of jaw frame 122. Since slots 117 of flags 115 of jaw frame 112 are disposed at an oblique angle relative to slots 127 of flags 125 of jaw frame 122, distal translation of pin 104 urges jaw frame 112 to pivot about pivot pin 102 relative to jaw frame 122 from the spaced-apart position toward the approximated position. On the other hand, when drive bar 130 is translated distally, e.g., when moveable handle 40 is released, pin 104 is translated distally along slots 117, 127 to urge jaw frame 112 to pivot about pivot pin 102 relative to jaw frame 122 from the approximated position back to the spaced-apart position. As can be appreciated, the double-flagged configuration of jaw frames 112, 122 and the double pin configuration of end effector assembly 100 both help provide structural stability and support to end effector assembly 100 as jaw members 110, 120 are moved between the spaced-apart and approximated positions and as jaw members 110, 120 are retained in either the spaced-apart or approximated position.

Figure 5:
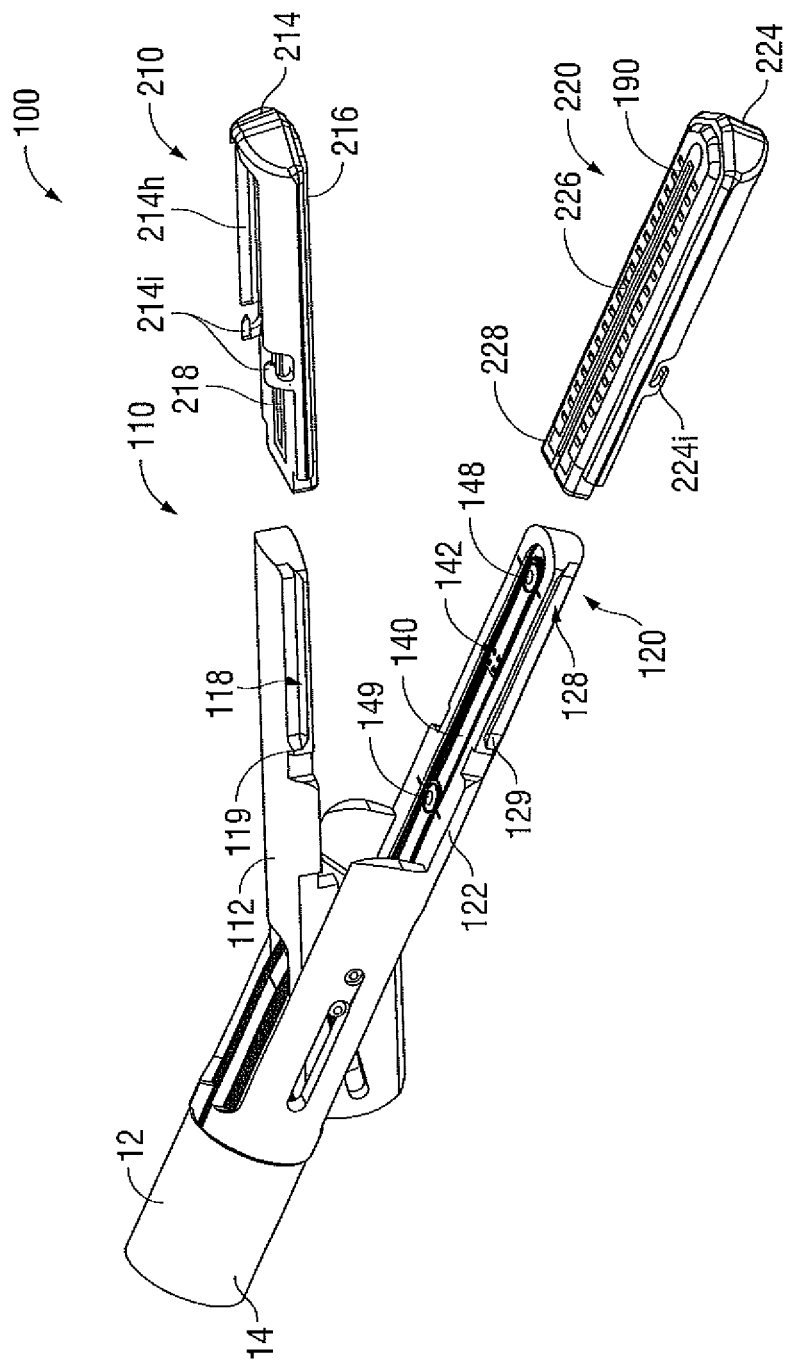
FIG. 5 is a front, perspective view of the end effector assembly of FIG. 2 wherein first and second replaceable components of the first and second jaw members, respectively, have been removed.

Referring now to FIGS. 4-5, flex circuit 140 of jaw member 120 will be described. Flex circuit 150 of jaw member 110 is substantially similar to flex circuit of jaw member 120 and, thus, will not be substantially described herein for purposes of brevity. Further, as mentioned above, although each of jaw members 110, 120 is shown including a flex circuit 150, 140, respectively, only one of jaw members 110, 120 need include a flex circuit 150, 140, respectively. Flex circuit 140, as best shown in FIG. 4, defines a generally flat, elongated configuration having a distal segment 143, an intermediate segment 144 and a proximal segment 145. Flex circuit 140 may be formed from a flexible material, e.g., a flexible polymer, allowing flex circuit 140 to be bent in a vertical direction without effecting the operation of flex circuit 140. Further, intermediate segment 144 of flex circuit 140, which is disposed adjacent the pivot point of jaw members 110, 120, may include one or more flex members 146 configured to facilitate flexing of flex circuit 140 upon movement of jaw members 110, 120 between the spaced-apart and approximated positions. Such a feature is particularly advantageous in embodiments where end effector assembly 100 is defined as a bilateral assembly, e.g., where both jaw members 110, 120 are moveable relative to shaft 12, or in unilateral embodiments where jaw member 120 is the moveable jaw member. As can be appreciated, flex circuit 150 also includes a distal segment 153, an intermediate segment 154 and a proximal segment 155. Intermediate segment 154 of flex circuit 150 of jaw member 110 likewise includes flex members 156 to facilitate flexing of flex circuit 150 as jaw member 110 is moved relative to jaw member 120 between the spaced-apart and approximated positions.

With continued reference to FIGS. 4-5, flex circuit 140 is substantially encased within an insulative covering 147. However, flex circuit 140 includes one or more exposed electrical contacts, e.g., first electrical contact 148 and second electrical contact 149, disposed on distal segment 143 thereof for electrically coupling to tissue sealing plate 226 and/or electrical cutting insert 190, as will be described in greater detail below. Proximal segment 145 of flex circuit 140 may be adhered, laser-welded, or otherwise secured within recess 142 of jaw frame 122 with first and second electrical contacts 148, 149, respectively, facing upwardly therefrom, as shown in FIG. 5. Flexible circuit 140 may also be releasably secured within recess 142 of jaw frame 122, such that flexible circuit 140 may be replaced or interchanged with new and/or different flex circuits 140. For example, it may be desirable to select a different flex circuit 140, e.g., a flex circuit having greater or fewer electrical contacts or electrical contacts disposed in different positions, depending on the particular procedure to be performed or the particular configuration of the replaceable component 220 to be secured to jaw frame 122. Distal segment 143 of flexible circuit 140 may be releasably couplable to intermediate segment 144 of flexible circuit 140 to permit replacement of distal segment 143, or, alternatively, the entire flexible circuit 140 may be replaceable. As can be appreciated, the flexible configuration of flex circuit 140 (and flex circuit 150) facilitates installation, removal and replacement of flex circuit 140 from jaw frame 122 of end effector assembly 100.

Proximal segment 145 of flex circuit 140 is configured to extend proximally from jaw frame 122 of jaw member 120 into shaft 12, ultimately coupling to cable 310 (FIG. 1) which, in turn, is coupled to a source of electrosurgical energy (not explicitly shown), or coupling to the battery (not shown) disposed within housing 20, in embodiments where forceps 10 is a battery-powered device. Further, proximal segment 145 may extend completely through shaft 12 and into housing 20 (FIG. 1), or may extend only partially into shaft 12. In either configuration, proximal segment 145 may be releasably couplable to the source of electrosurgical energy, e.g., via the wire(s) (not explicitly shown) of cable 310 (FIG. 1), to permit replacement of flex circuit 140.

Figure 6A:
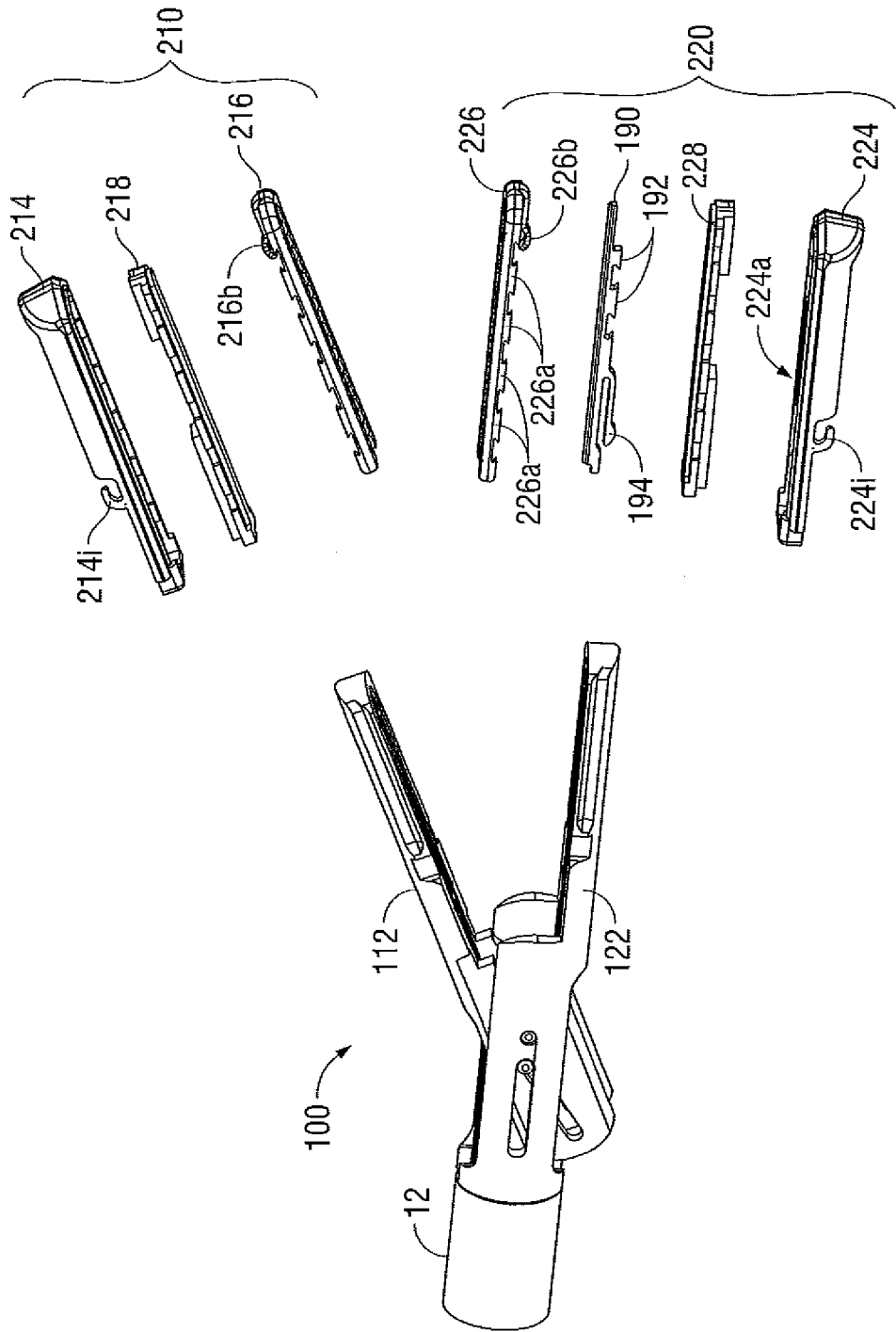
FIG. 6A is a front, perspective view of the end effector assembly of FIG. 2 wherein the first and second replaceable components of the first and second jaw members, respectively, are shown with parts separated.
Figure 6B:
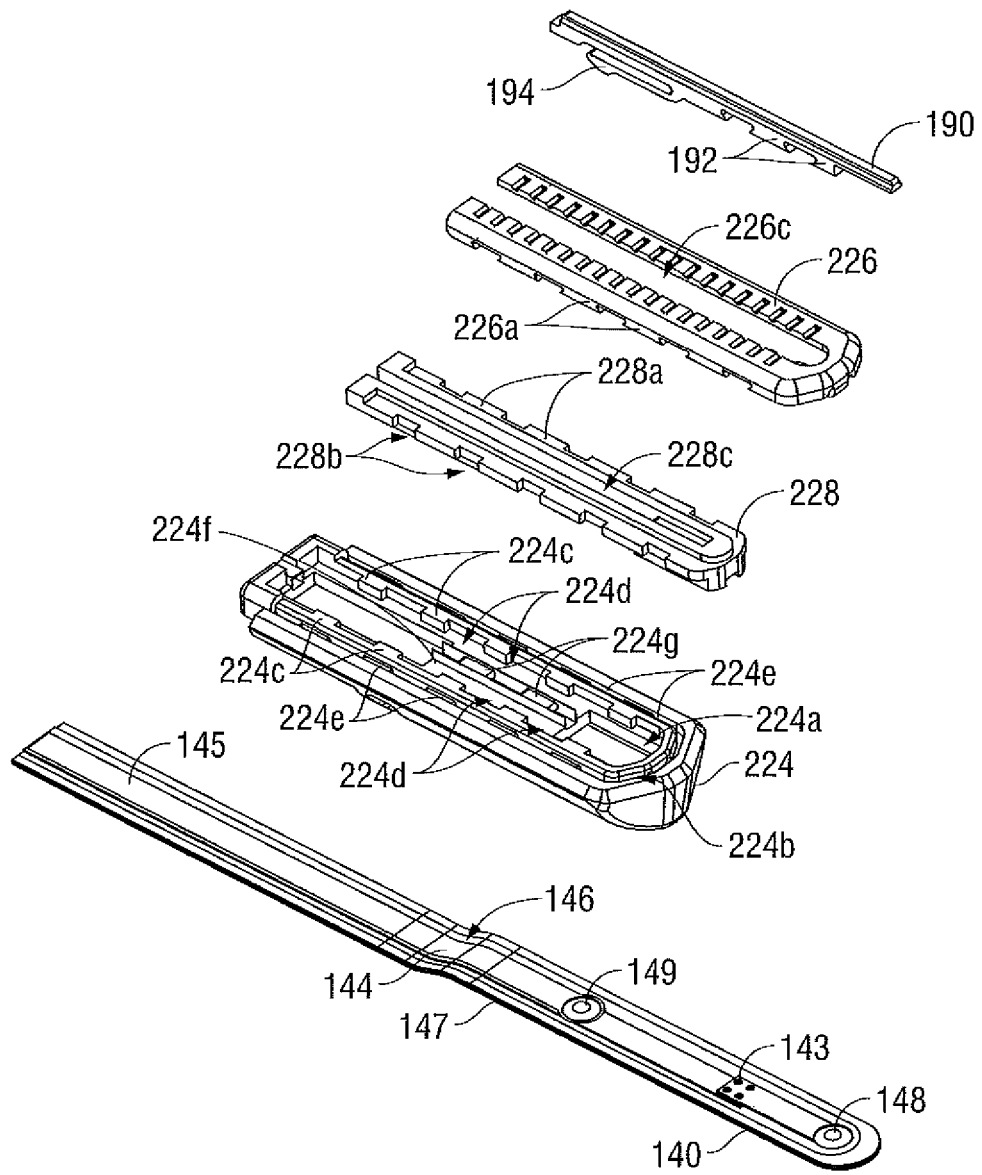
FIG. 6B is a front, perspective view of one of the jaw members of the end effector assembly of FIG. 2 wherein the jaw member is shown with parts separated.
Figure 7:
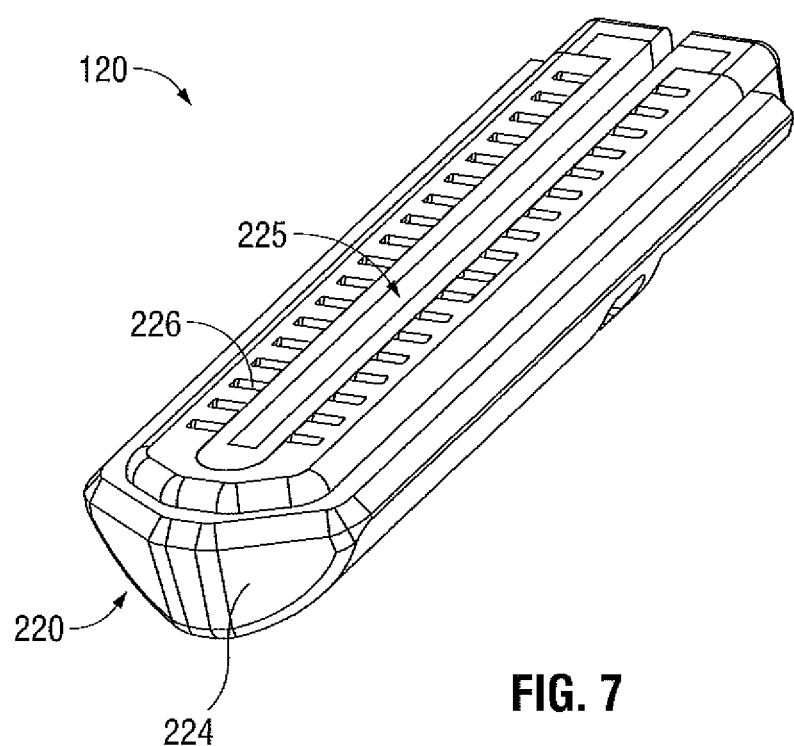
FIG. 7 is a front, perspective view of one of the jaw members of the end effector assembly of FIG. 2 shown in a mechanical cutting mode.

Referring now to FIGS. 5-6B, as mentioned above, jaw members 110, 120 of end effector assembly 100 each include a replaceable component 210, 220, respectively, that is releasably engageable with the respective jaw frame 112, 122. Replaceable components 210, 220 are removable from jaw frames 112, 122, respectively, and are replaceable with new replaceable components 210, 220, e.g., replaceable components 210, 220 may be configured to be discarded and replaced after a single use (or a single procedure), while the remaining components of forceps 10 may be formed from a sterilizable material such that they may be sterilized, e.g., placed in an autoclave (not shown), after each procedure for repeated use. Alternatively, the remaining components of forceps 10 may likewise be replaceable and/or disposable. For example, flex circuits 150, 140 of jaw frames 112, 122, respectively, as mentioned above, may be configured to be replaced after each use, or a particular flex circuit 150, 140 may be selected for use in accordance with the particular surgical procedure to be performed. In either embodiment, e.g., where replaceable components 210, 220 and/or flex circuits 150, 140 are disposable or reusable, the ability to interchange the components of end effector assembly 100 is advantageous in that the user may select the components for use with forceps 10 that are best suited for the particular procedure to be performed, without requiring an entirely new surgical instrument. Further, as can be appreciated, requiring only a new set of replaceable components 210, 220 (and/or flex circuits 150, 140), rather than an entire new surgical instrument, helps reduce the equipment costs associated with performing a particular surgical procedure.

With continued reference to FIGS. 5-6B, replaceable components 210, 220 of jaw members 110, 120, respectively, each include an outer jaw housing 214, 224, an electrically conductive tissue sealing plate 216, 226, and an insulator 218, 228 configured to electrically isolate tissue sealing plates 216, 226 from outer jaw housings 214, 224, respectively. Further, one (or both) of replaceable components 210, 220, e.g., replaceable component 220, may include an electrical cutting insert 190 releasably engageable therewith, while the other replaceable component 210, 220, e.g., replaceable component 210, may include an insulting insert 198 (see FIG. 2) releasably engageable therewith, as will be described in greater detail below. Other configurations are also contemplated, e.g., where electrical cutting insert 190 is fixed within replaceable component 220 and/or where insulting insert 198 (see FIG. 2) is fixed within replaceable component 210. The subcomponents of replaceable components 210, 220 are substantially similar and, thus, only those subcomponents of replaceable component 220 and the differences between replaceable components 210, 220 will be described herein for purposes of brevity.

Outer jaw housing 224 of replaceable component 220 is configured to house insulator 228 therein and to engage tissue sealing plate 226 thereon. In particular, outer jaw housing 224 defines an internal passageway 224a configured to receive insulator 228 therein and an outer channel 224b extending about the outer periphery of internal passageway 224a that is configured to receive a portion of tissue sealing plate 226 therein. More specifically, outer jaw housing 224 includes a series of alternating tabs 224c and recesses 224d on an internal surface thereof that defines internal passageway 224a. Likewise, insulator 228 includes a series of complementary alternating tabs 228a and recesses 228b on an outer periphery thereof such that, upon insertion of insulator 228 into internal passageway 224a of outer jaw housing 224, tabs 224c, 228a and recesses 224d, 228b, engage one another to inhibit substantial movement of insulator 228 relative to jaw housing 224. Alternatively, insulator 228 may be overmolded within jaw housing 224 to define complementary tabs 228a and recesses 228b as a result of the tabs 224c and recesses 224d formed within jaw housing 224.

As shown in FIGS. 6A-6B, outer channel 224b of outer jaw housing 224 includes a plurality of spaced-apart slots 224e, each of which is configured to receive a downwardly extending flange 226a of tissue sealing plate 226. Downwardly-extending flanges 226a of tissue sealing plate 226 may taper from the free ends to the fixed ends thereof, as best shown in FIG. 6A, such that flanges 226a are resiliently compressed upon insertion into slots 224e and "snap" into engagement therewith to secure tissue sealing plate 226 about outer jaw housing 224, although overmolding is also contemplated. Further, in the assembled condition of replaceable component 220, distal finger 226b of tissue sealing plate 226, which projects downwardly from tissue sealing plate 226, extends through longitudinal channel 228c of insulator 228 and internal passageway 224a of outer jaw housing 224, the importance of which will be described below.

With continued reference to FIGS. 6A-6B, with insulator 228 disposed within outer jaw housing 224 and with tissue sealing plate 226 secured thereto, longitudinal channel 228c defined within insulator 228 and blade channel 226c defined within tissue sealing plate 226 are substantially aligned with one another to form blade channel 225 (see FIGS. 8A-8C). Such a configuration permits, in a mechanical cutting mode of forceps 10, reciprocation of knife blade 182 (see FIGS. 8A-8C) through blade channel 125 of jaw member 120 (and/or blade channel 115 of jaw member 110) (see FIGS. 8A-8C) for cutting tissue grasped between jaw members 110, 120, as will be described in greater detail below. Outer jaw housing 224 also includes a shelf 224f disposed within internal passageway 224a that has one or more engagement features 224g configured to receive corresponding engagement features 192 extending from electrical cutting insert 190. Engagement features 192 may be in the form of tapered tabs, similar to those discussed above with respect to tissue sealing plate 226, such that corresponding tabs 192 of electrical cutting insert 190 may be snap-fittingly engageable with engagement features, or slots 224g of shelf 224f of outer jaw housing 224 to releasably secure electrical cutting insert 190 within longitudinal channel 228c of insulator 228 and blade channel 226c of tissue sealing plate 226. Alternatively, in embodiments where electrical cutting insert 190 is fixed jaw housing 224, electrical cutting insert 190 may be fixed therein via overmolding. Electrical cutting insert 190 is formed at least partially from an electrically conductive material and is configured to be positioned within and to extend at least partially from blade channel 226c of tissue sealing plate 226, for use in an electrical cutting mode of forceps 10. Further, similar to distal finger 226b of tissue sealing plate 226, proximal finger 194 of electrical cutting insert 190, which projects downwardly from electrical cutting insert 190, extends through longitudinal channel 228c of insulator 228 and internal passageway 224a of outer jaw housing 224, the importance of which will be described below.

Replaceable component 210 of jaw member 110, as mentioned above, and as shown in FIG. 6A, similarly includes an outer jaw housing 214, an insulator 218, and a tissue sealing plate 216. Insulator 218 of replaceable component 210 may include a longitudinal channel (not explicitly shown) defined therethrough and tissue sealing plate 216 of replaceable component 210 may include a blade channel (not explicitly shown) defined therethrough that cooperate to form blade channel 215 (FIGS. 8A-8C). As mentioned above, blade channel 215 (FIGS. 8A-8C) of replaceable component 210 may cooperate with blade channel 225 (FIGS. 8A-8C) of replaceable component 220 to permit reciprocation of knife blade 182 (FIGS. 8A-8C) therethrough, or, alternatively, one of jaw members 110, 120, e.g., jaw member 110, may define a continuous tissue sealing plate 216 such that knife blade 182 (FIGS. 8A-8C) extends through only one of jaw members 110, 120, e.g., jaw member 120. Additionally, an electrical cutting insert 190 may be engaged within either or both of jaw members 110, 120, similarly as described about with respect to jaw member 120, or may be engaged within only one of jaw members 110, 120, e.g., jaw member 120, while the other jaw member, e.g., jaw member 110, defines a continuous tissue sealing plate or includes an insulating insert 198 (see FIG. 2) disposed within the blade channel 215 (FIGS. 8A-8C) thereof.

Turning back to FIG. 5, replaceable components 210, 220 of jaw members 110, 120, respectively, are slidably positionable about jaw frames 112, 122, respectively, to secure replaceable components 210, 220 thereon. More specifically, jaw frames 112, 122 each include a pair of lateral wings 118, 128, respectively, that are slidably received within longitudinal groove 214h of outer jaw housing 214 of replaceable component 210 and a longitudinal groove (not shown), similar to longitudinal groove 214h, defined within outer jaw housing 224 of replaceable component 220, respectively, as replaceable components 210, 220 are slid proximally over jaw frames 112, 122, respectively. Outer jaw housings 214, 224 each further include a pair of tangs 214i, 224i, respectively, disposed on opposite sides thereof that are configured to engage complementary stops 119, 129, respectively, disposed on opposite sides of jaw frames 112, 122, respectively, e.g., in snap-fit engagement therewith, to secure replaceable components 210, 220 about jaw frames 112, 122. More particularly, as best shown in FIG. 5, outer jaw housings 214, 224 of replaceable components 210, 220, respectively, each include a pair of tangs 214i, 224I, respectively, that are configured to engage complementary stops 119, 129, respectively, defined on respective jaw frames 112, 122. Upon slidable positioning of replaceable components 210, 220 about jaw frames 112, 122, respectively, tangs 214i, 224i are flexed outwardly about stops 119, 129, respectively, and snap into engagement therewith to secure replaceable components 210, 220 on jaw frames 112, 122, respectively. Alternatively, any other suitable engagement member(s) or engagement mechanisms may be provided.

Continuing with reference to FIG. 5, tangs 214i, 224i of outer jaw housings 214, 224 of replaceable components 210, 220, respectively, may be configured to transition between a new state and a used state upon the initial use of replaceable components 210, 220, ensuring that replaceable components 210, 220 are single-use only components. In the new state, replaceable components 210, 220 may be engaged to jaw frames 112, 122, respectively, e.g., in the new state, tangs 214i, 224i and stops 119, 129, respectively, define complementary configurations. However, in the used state, replaceable components 210, 220 are inhibited from being engaged to jaw frames 112, 122, respectively, e.g., in the used state, tangs 214i, 224i, are rendered incompatible with stops 119, 129, respectively. In particular, tangs 214i, 224i may be altered, or deformed upon engagement with stops 119, 129, respectively, e.g., upon engagement of replaceable components 210, 220 with respective jaw frames 112, 122, to inhibit repeated engagement of replaceable components 210, 220 with jaw frames 112, 122, respectively. For example, as tangs 214i, 224i are flexed laterally about stops 119, 129 during slidable positioning of replaceable components 210, 220 about jaw frames 112, 122, respectively, tangs 214i, 224i may be bent, cracked, snapped, or otherwise uni-directionally destroyed, e.g., a portion or portions thereof may be mechanically altered, such that tangs 214i, 224i are capable of sufficiently securing replaceable components 210, 220 about jaw frames 112, 122, but are inhibited from being re-engaged to stops 119, 129, respectively. Tangs 214i, 224i, may alternatively be similarly bent, cracked, snapped, or otherwise uni-directionally destroyed as tangs 214i, 224i, are flexed laterally outwardly during disengagement of replaceable components 210, 220 from jaw frames 112, 122, respectively, thus transitioning replaceable components 210, 220 from the new state to the used state upon disengagement from jaw frames 112, 122, respectively. In either embodiment, as can be appreciated, reuse of replaceable components 210, 220 is substantially inhibited in that once removed, replaceable components 210, 220 would no longer be capable of being re-engaged to jaw frames 112, 122, respectively. Further, tangs 214i, 224i may otherwise be electrically or electro-mechanically altered in any other suitable fashion to prevent re-use of replaceable components 210, 220.

With continued reference to FIG. 5, replaceable components 210, 220 may alternatively be configured to transition from the new state to the used state upon use of forceps 10. More specifically, as will be described in greater detail below, and as mentioned above, jaw members 110, 120 are adapted to connect to a source of electrosurgical energy (not explicitly shown) for conducting energy through tissue grasped between jaw members 110, 120 to effect a tissue seal. As can be appreciated, a certain amount of heat is created during the tissue sealing process. As such, tangs 214i, 224i, of replaceable components 210, 220, respectively, may be formed at least partially of a relatively low-melting point material such that the heat created during the tissue sealing process is sufficient to alter a portion of tangs 214i, 224i, thereby transitioning tangs 214i, 224i from the new state to the used state. Thus, after the initial tissue sealing process, replaceable components 210, 220 are rendered incapable of being re-engaged to jaw frames 112, 122, respectively. More particularly, tangs 214i, 224i may melt into an altered or non-compatible configuration, or may include a fusible linkage (not explicitly shown) that melts in order to transition tangs 214i, 224i into a non-compatible configuration in order to transition replaceable components 210, 220 from the new state to the used state. Other one-way features configured to transition replaceable components 210, 220 from a new state to a used state may alternatively or additionally be provided.

Referring now to FIGS. 1-2 and 7-9B, the use and operation of forceps 10 will be described. Initially, as described above, flex circuits 150, 140 are coupled to a source of electrosurgical energy (not explicitly shown) and are positioned within jaw frames 112, 122, respectively. Next, replaceable components 210, 220 are assembled, as discussed above, and are engaged on respective jaw frames 112, 122 of jaw members 110, 120. More specifically, as replaceable components 210, 220 are slid proximally about jaw frames 112, 122 into engagement thereon, distal fingers 216b, 226b of tissue sealing plates 216, 226, respectively, are translated into position adjacent the first electrical contacts of flex circuits 150, 140, respectively, e.g., distal finger 226b is translated into contact with first contact 148 of flex circuits 140 (and similarly with regard to the corresponding components of tissue sealing plate 216 and flex circuit 150), such that tissue sealing plates 216, 226, are electrically coupled to flex circuits 150, 140, respectively. Fingers 216b, 226b of tissue sealing plates 216, 226, respectively, may be configured to be resiliently deflected upon engagement of replaceable components 210, 220 and jaw frames 112, 122 such that fingers 216b, 226b are resiliently biased into contact with flex circuits 150, 140, respectively, ensuring electrical coupling therebetween. As can be appreciated, this configuration permits electrosurgical energy to be supplied to tissue sealing plate 216 and/or tissue sealing plate 226 of jaw members 110, 120, respectively, to seal tissue grasped therebetween.

Turning now to FIGS. 1, 7 and 8A-8C, at this point, blade channels 215, 225 of jaw members 110, 120, respectively, remain empty, or unfilled. This configuration corresponds to the mechanical cutting mode of forceps 10. In use, as shown in FIG. 8A, with jaw members 110, 120 disposed in the spaced-apart position, end effector assembly 100 is maneuvered into position such that tissue to be grasped, sealed, and or cut, is disposed between jaw members 110, 120. Next, moveable handle 40 is pulled proximally relative to fixed handle 50 such that jaw member 110 is pivoted relative to jaw member 120 from the spaced-apart position to the approximated position to grasp tissue therebetween (see FIG. 8B). Thereafter, electrosurgical energy may be supplied, e.g., via activation of actuator 92, to tissue sealing plate 216 and/or tissue sealing plate 226 (e.g., via flex circuits 150, 140, respectively) and conducted through tissue to effect a tissue seal. As shown in FIG. 80, knife blade 182 may then be advanced from the retracted position (FIG. 8B) to the extended position (FIG. 8C), e.g., via activation of trigger 82, and through blade channels 215, 225 jaw members 110, 120, respectively, to cut the previously sealed tissue grasped between jaw members 110, 120.

Figure 9A:
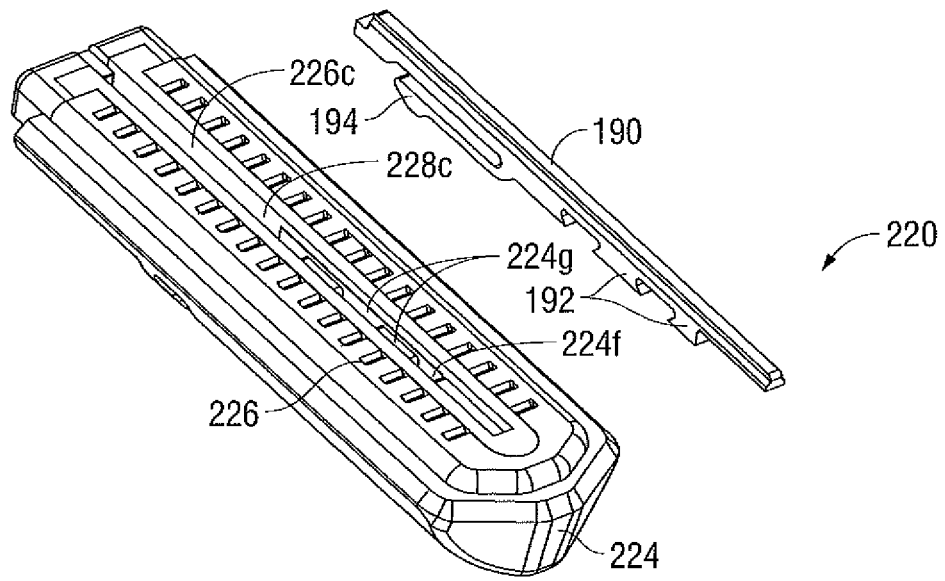
FIG. 9A is a front, perspective view of one of the jaw members of the end effector assembly of FIG. 2 including an electrical cutting insert configured for positioning therein.
Figure 9B:
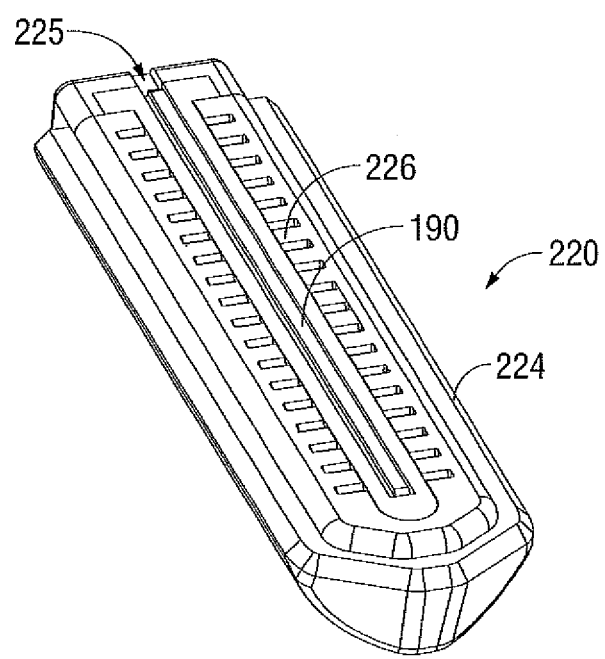
FIG. 9B is a front, perspective view of the jaw member of FIG. 9A shown in an electrical cutting mode.

On the other hand, as shown in FIGS. 1-2 and 9A-9B, forceps 10 may alternatively be used for grasping, sealing and/or cutting tissue in an electrical cutting mode. In the electrical cutting mode, as best shown in FIGS. 9A-9B, electrical cutting insert 190 is snap-fit, or otherwise engaged to shelf 224*f* (FIG. 6B) of outer jaw housing 224 within longitudinal channel 228*c* (see FIG. 6B) of insulator 228 (see FIG. 6B) and blade channel 226*c* (FIG. 6B) of tissue sealing plate 226 (collectively blade channel 225) of jaw member 120, although electrical cutting insert 190 may alternatively be molded or otherwise fixed within blade channel 225. More particularly, upon insertion of electrical cutting insert 190 into blade channel 225, proximal finger 194 of electrical cutting insert 190 is moved into position adjacent to and in electrical communication with second electrical contact 149 of flex circuit 140 such that electrosurgical energy may be supplied to electrical cutting insert 190 to electrically cut tissue grasped between jaw members 110, 120. Similar to finger 226*b* of tissue sealing plate 226 (FIG. 6B), finger 194 of electrical cutting insert 190 may be configured to be resiliently deflected upon engagement within jaw member 120 to bias finger 194 into electrical communication with flex circuit 140. Further, electrical contacts 148, 149 of flex circuit 140 may be independent of one another, such that electrosurgical energy may be independently supplied to tissue sealing plate 226 and/or electrical cutting insert 190, e.g., such that actuator 92 is operable to supply electrosurgical energy to tissue sealing plate 226, while actuator 96 is independently operable to supply electrosurgical energy to electrical cutting insert 190.

In use, end effector assembly 100 is maneuvered into position such that tissue to be grasped, sealed, and or cut, is disposed between jaw members 110, 120. Next, moveable handle 40 is pulled proximally relative to fixed handle 50 such that jaw member 110 is pivoted relative to jaw member 120 from the spaced-apart position to the approximated position to grasp tissue therebetween. Thereafter, electrosurgical energy may be supplied, e.g., via activation of actuator 92, to tissue sealing plate 216 and/or tissue sealing plate 226 and conducted through tissue to effect a tissue seal. Next, electrical cutting insert 190 may be activated, e.g., via activation of actuator 96, to conduct energy through tissue to cut the previously sealed tissue grasped between jaw members 110, 120.

As discussed above, upon engagement of replaceable components 210, 220 with jaw frames 112, 122, respectively, upon disengagement of replaceable components 210, 220 from jaw frames 112, 122, respectively, and/or upon use of end effector assembly 100, e.g., upon application of electrosurgical energy to jaw members 110, 120, replaceable components 210, 220 may be transitioned from a new state to a used state. Accordingly, after the initial use and subsequent removal of replaceable components 210, 220 from jaw frames 112, 122, respectively, replaceable components 210, 220 can no longer be engaged to jaw frames 112, 122 and, thus are inhibited from being re-used. As such, once the reusable components of forceps 10 have been sterilized or otherwise prepared for re-use, a new set of replaceable components 210, 220 for positioning about jaw frames 112, 122, respectively, are required.

Turning now to FIGS. 10-13B, another embodiment of an end effector assembly configured for use with forceps 10 (FIG. 1) is shown generally identified by reference numeral 1000. End effector assembly 1000 is similar to end effector assembly 100 (see FIGS. 1-2) and includes first and second jaw members 1100, 1200, respectively, that are pivotable relative to one another between a spaced-apart position and an approximated position for grasping tissue therebetween. Each jaw member 1100, 1200 includes a fixed jaw frame 1120, 1220, respectively, and a replaceable component 2100, 2200 that is engageable with fixed jaw frame 1120, 1220, respectively. As best shown in FIG. 11A and 11B, jaw frames 1120, 1220 each include a electrical contact pin 1300, 1400, e.g., a male electrical connector 1300, 1400, extending from a distal end 1140, 1240, respectively, thereof, although only one of jaw frames 1120, 1220 need include an electrical contact pin 1300, 1400, respectively. One or both of electrical contact pins 1300, 1400 is adapted to connect to a source of electrosurgical energy (not explicitly shown) for supplying electrosurgical energy to one or both of jaw members 1100, 1200. Further, each jaw frame 1120, 1220 defines a generally trapezoidal-shaped cross-sectional configuration, although jaw frames 1120, 1220 may define other suitable configurations. Each jaw frame 1120, 1220 also includes a pair of lateral flanges 1160, 1260, respectively, configured to engage replaceable components 2100, 2200, respectively, to secure replaceable components 2100, 2200 thereon.

Figure 11A:
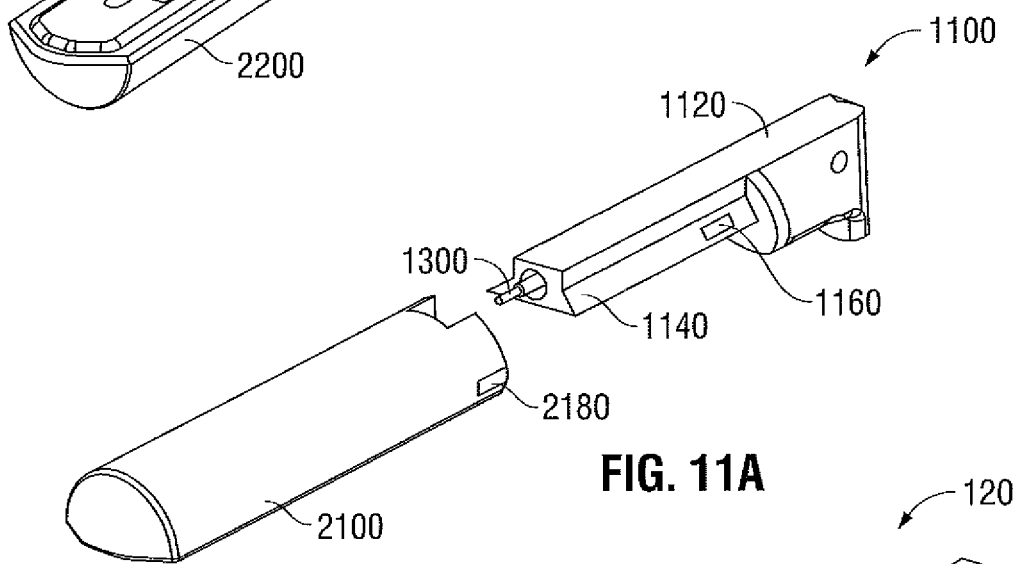
FIG. 11A is a front, perspective view of one of the jaw members of the end effector assembly of FIG. 10 shown with parts separated.
Figure 11B:
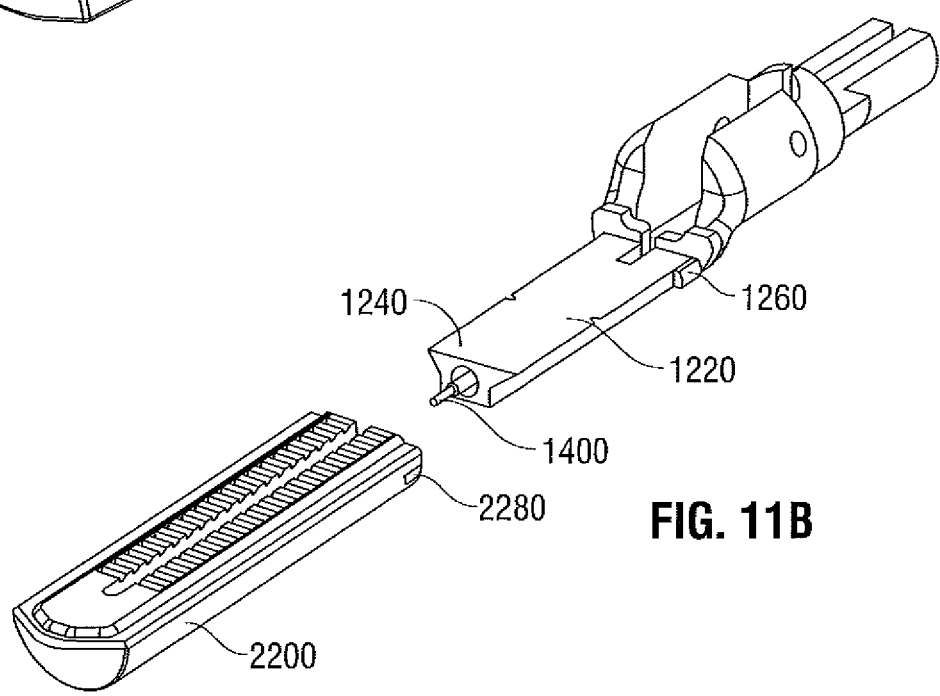
FIG. 11B is a front, perspective view of the other jaw member of the end effector assembly of FIG. 10 shown with parts separated.
Figure 12:
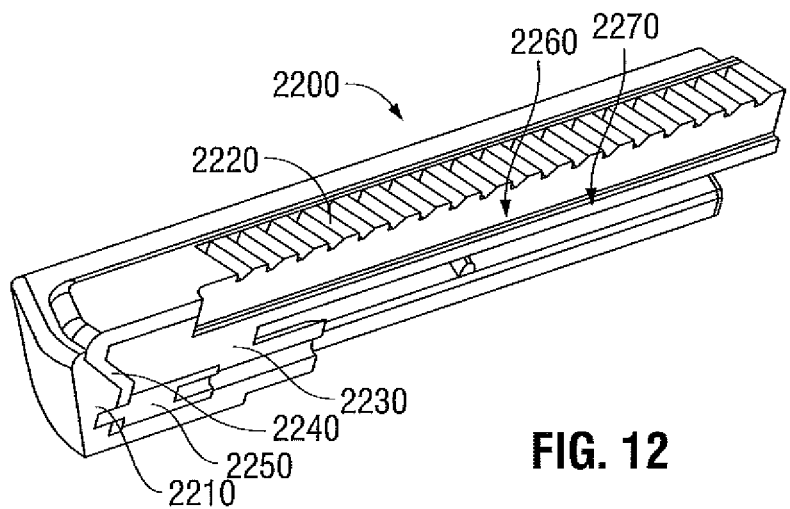
FIG. 12 is a longitudinal, cross-sectional view of one of the jaw members of the end effector assembly of FIG. 10.

Referring now to FIG. 12, in conjunction with FIG. 11B, replaceable component 2200 and the assembly of jaw member 1200 will be described. The configuration and assembly of replaceable component 2100 of jaw member 1100 is similar to that of replaceable component 2200 jaw member 1200 and thus will not be repeated here for purposed of brevity. Replaceable component 2200, as best shown in FIG. 12, includes an outer jaw housing 2210, an electrically conductive tissue sealing plate 2220, and an insulator 2230 configured to electrically isolate tissue sealing plate 2220 from outer jaw housing 2210. Outer jaw housing 2210 of replaceable component 2200 houses insulator 2230 therein and engages tissue sealing plate 2220 thereon. More specifically, tissue sealing plate 2220 is positioned about outer jaw housing 2210 to define an opposed tissue sealing surface in conjunction with tissue sealing plate 1220 of replaceable component 2100 of jaw member 1100 (see FIGS. 10, 11A and 13A), while insulator 2230 is disposed between outer jaw housing 2210 and tissue sealing plate 2220. Tissue sealing plate 2220 further includes a distal flange 2240 extending downwardly therefrom into outer jaw housing 2210 and into communication with female electrical connection hub 2250. Flange 2240 of tissue sealing plate 2220 may surround, abut, or may otherwise be disposed in electrical communication with female electrical connection hub 2250 disposed within outer jaw housing 2210. As can be appreciated, female electrical connection hub 2250 is formed at least partially from an electrically conductive material such that electrosurgical energy may be supplied therethrough to tissue sealing plate 2220. Outer jaw housing 2210 further includes an internal cavity defining a complementary configuration relative to jaw frame 1220, e.g., a trapezoidal-shaped cross-sectional configuration, to facilitate insertion and engagement of jaw housing 2210 and jaw frame 1220 to one another.

Figure 10:
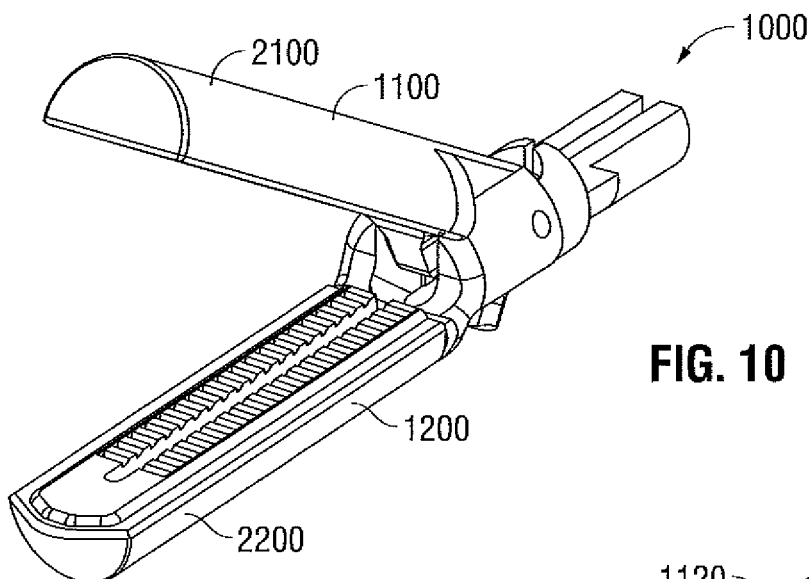
FIG. 10 is a front, perspective view of another embodiment of an end effector assembly configured for use with the forceps of FIG. 1.

With continued reference to FIG. 12, in conjunction with FIG. 10, tissue sealing plate 2220 includes a longitudinally-extending blade channel 2260 defined therein and insulator 2230 includes a longitudinal channel 2270 defined therein that is aligned within blade channel 2260 of tissue sealing plate 2220 to permit reciprocation of a knife blade 182 (see FIGS. 8A-8C) therethrough for cutting tissue grasped between jaw members 1100, 1200. Similar to end effector assembly 100 discussed above (see FIGS. 1-9B), tissue sealing plate 2220 and insulator 2230 of replaceable component 2200 may also be configured to receive an electrical cutting insert 2300 (FIG. 13B) therein for electrically cutting tissue, or may come integrally assembled with electrical cutting insert 2300 (FIG. 13B) disposed therein, as will be described below.

In order to engage replaceable components 2100, 2200 about jaw frames 1120, 1220, respectively, replaceable components 2100, 2200 are slid proximally over jaw frames 1120, 1220, respectively, until lateral flanges 1160, 1260, of jaw frames 1120, 1220, respectively, snap into engagement with respective slots 2180, 2280 defined within replaceable components 2100, 2200, respectively. As replaceable components 2100, 2200 are slid proximally into engagement about jaw frames 1120, 1220, respectively, electrical contact pin 1400 of jaw frame 1220 is inserted into female connection hub 2250 of replaceable component 2200, thereby electrically coupling tissue sealing plate 2220 to the source of electrosurgical energy (not explicitly shown). Similarly, electrical contact pin 1300 of jaw frame 1120 is inserted into a corresponding connection hub (not shown) disposed within replaceable component 2100 of jaw member 1100. Slots 2180, 2280 of replaceable components 2100, 2200, respectively, may be configured as single-use elements, e.g., slots 2180, 2280 may be transitioned from a new state to a used state upon engagement thereof, disengagement thereof, and/or use of end effector assembly 1000, similarly to any of the embodiments discussed above with respect to end effector assembly 100 to inhibit reengagement of replaceable components 2100, 2200 to jaw frames 1120, 1220, respectively, after the initial use.

Figure 13A:
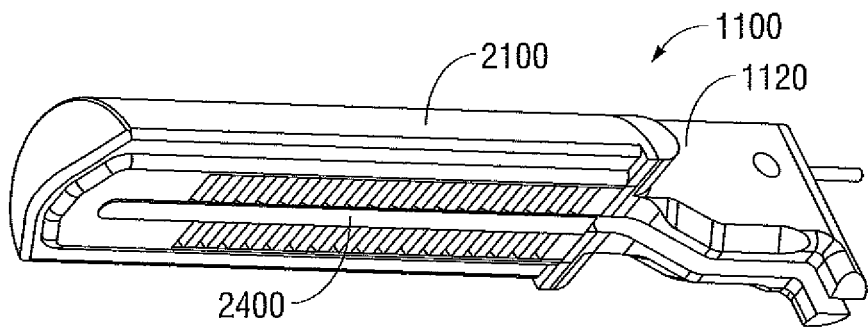
FIG. 13A is a rear, perspective view of one of the jaw members of the end effector assembly of FIG. 10 shown in an assembled condition in an electrical cutting mode.
Figure 13B:
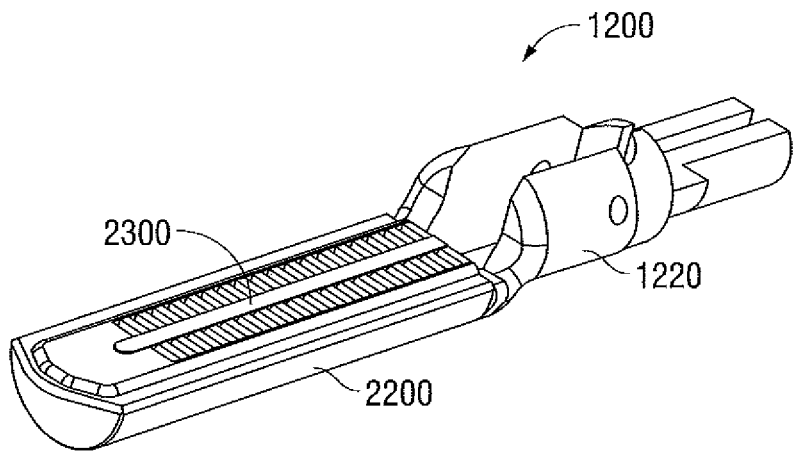
FIG. 13B is a front, perspective view of the other jaw member of the end effector assembly of FIG. 10 shown in an assembled condition in an electrical cutting mode.

Referring now to FIGS. 13A-13B, replaceable component 2100 and/or replaceable component 2200 may be configured as electrical cutting components. More specifically, an electrical cutting member 2300 may be engaged within either or both of jaw members 1100, 1200, similarly as described above with respect to end effector assembly 100 (see FIGS. 9A-9B), or may be engaged within only one of jaw members 1100, 1200, e.g., jaw member 1200, while the other jaw member, e.g., jaw member 1100, defines a continuous tissue sealing plate or includes an insulating member 2400 disposed therein and configured to oppose electrical cutting member 2300 of jaw member 1200. The electrical cutting components, e.g., electrical cutting member 2300 and/or insulating member 2400, may be integrally formed with replaceable components 2200, 2100, respectively, or may be removably engageable therewith. The use and operation of end effector assembly 1000 is similar to that of end effector assembly 100 described above and, thus, will not be repeated herein. Further, any of the features or embodiments of end effector assembly 100 (FIGS. 1-9B) and/or end effector assembly 1000 (FIGS. 10-13B) described herein may similarly be adapted for use with the other end effector assembly 100, 1000.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   an end effector assembly including first and second jaw members, at least one of the first and second jaw members moveable relative to the other between a spaced-apart position and an approximated position for grasping tissue therebetween, at least one of the first and second jaw members including:
   a jaw frame including an engagement recess defined on each lateral side thereof;
   an electrical connection member disposed on the jaw frame and adapted to connect to a source of electrosurgical energy, the electrical connection member including an insulative covering disposed thereabout and a first exposed electrical contact; and
   a replaceable component configured for slidable positioning about the jaw frame, the replaceable component including:
   an outer jaw housing having an engagement tang disposed on each lateral side thereof, the engagement tangs configured to engage the engagement recesses of the jaw frame upon slidable positioning of the replaceable component about the jaw frame to secure the replaceable component to the jaw frame; and
   an electrically conductive tissue sealing plate engaged to the outer jaw housing to define a tissue sealing surface, the electrically conductive tissue sealing plate including a finger extending into the outer jaw housing, wherein, upon slidable positioning of the replaceable component about the jaw frame to secure the replaceable component to the jaw frame, the finger is translated along the insulative covering and into contact with the first exposed electrical contact to electrically couple the electrically conductive tissue sealing plate with the electrical connection member.

2. The forceps according to claim 1, wherein the tissue sealing plate and the outer jaw housing each include a plurality of complementary protrusions and recesses such that the tissue sealing plate is configured to snap-fittingly engage the outer jaw housing.

3. The forceps according to claim 1, further comprising an insulator disposed within the outer jaw housing, the insulator configured to electrically isolate the tissue sealing plate from the outer jaw housing.

4. The forceps according to claim 3, wherein the insulator and the outer jaw housing each include a plurality of protrusions and recesses engageable with one another to retain the insulator in position within the outer jaw housing.

5. The forceps according to claim 1, further comprising a knife assembly including a knife blade, the knife blade longitudinally translatable relative to the jaw members between a retracted position and an extended position for cutting tissue grasped between the jaw members.

6. The forceps according to claim 1, further comprising an electrical cutting member engaged with the replaceable component, the electrical cutting member configured to electrically cut tissue grasped between the jaw members.

7. The forceps according to claim 6, wherein the electrical connection member includes a second exposed electrical contact and wherein the electrical cutting member includes a finger configured to electrically couple to the second exposed electrical contact of the electrical connection member upon slidable positioning of the replaceable component about the jaw frame to secure the replaceable component to the jaw frame.

8. The forceps according to claim 1, wherein the finger is resiliently flexible such that, upon slidable positioning of the replaceable component about the jaw frame to secure the replaceable component to the jaw frame, the finger is biased into contact with the first exposed electrical contact.

9. A end effector, comprising:
   an end effector assembly including first and second jaw members, at least one of the first and second jaw members moveable relative to the other between a spaced-apart position and an approximated position for grasping tissue therebetween, at least one of the first and second jaw members including:
   a jaw frame including at least one engagement member defined thereon and a flex circuit disposed thereon, the flex circuit adapted to connect to a source of electrosurgical energy, having an insulative covering disposed thereabout, and including a first exposed electrical contact; and
   a replaceable component configured for slidable positioning about the jaw frame, the replaceable component including:
   an outer jaw housing having at least one complementary engagement member configured to engage the at least one engagement member of the jaw frame upon slidable positioning of the replaceable component about the jaw frame to secure the replaceable component to the jaw frame; and
   an electrically conductive tissue sealing plate engaged to the outer jaw housing to define a tissue sealing surface, the electrically conductive tissue sealing plate including a finger extending into the outer jaw housing, wherein the finger is translated along the insulative covering and into contact with the first exposed electrical contact of the flex circuit upon slidable positioning of the replaceable component about the jaw frame to secure the replaceable component to the jaw frame.

10. The forceps according to claim 9, further comprising an insulator disposed within the outer jaw housing, the insulator configured to electrically isolate the tissue sealing plate from the outer jaw housing.

11. The forceps according to claim 9, further comprising a knife assembly including a knife blade, the knife blade longitudinally translatable relative to the jaw members between a retracted position and an extended position for cutting tissue grasped between the jaw members.

12. The forceps according to claim 9, further comprising an electrical cutting member engaged with the replaceable component, the electrical cutting member configured to electrically cut tissue grasped between the jaw members.

13. The forceps according to claim 12, wherein the flex circuit includes a second exposed electrical contact and wherein the electrical cutting member includes a finger configured to electrically couple to the second exposed electrical contact of the flex circuit upon slidable positioning of the replaceable component about the jaw frame to secure the replaceable component to the jaw frame.

14. The forceps according to claim 9, wherein the finger is resiliently flexible such that, upon slidable positioning of the replaceable component about the jaw frame to secure the replaceable component to the jaw frame, the finger is biased into contact with the first exposed electrical contact.

* * * * *